(12) United States Patent
Hearn et al.

(10) Patent No.: US 10,555,554 B2
(45) Date of Patent: Feb. 11, 2020

(54) SIMULATED CIGARETTE

(71) Applicant: Kind Consumer Limited, London (GB)

(72) Inventors: Alex Hearn, London (GB); Ritika Gupta, London (GB); Rene Mauricio Gonzalez Campos, London (GB); Khine Zaw Nyein, Middlesex (GB)

(73) Assignee: KIND CONSUMER LIMITED, London (GB)

( * ) Notice: Subject to any disclaimer, the term of this patent is extended or adjusted under 35 U.S.C. 154(b) by 591 days.

(21) Appl. No.: 14/777,733

(22) PCT Filed: Mar. 25, 2014

(86) PCT No.: PCT/GB2014/050939
§ 371 (c)(1),
(2) Date: Sep. 16, 2015

(87) PCT Pub. No.: WO2014/155093
PCT Pub. Date: Oct. 2, 2014

(65) Prior Publication Data
US 2016/0135500 A1 May 19, 2016

(30) Foreign Application Priority Data
Mar. 26, 2013 (GB) .................................. 1305494.5

(51) Int. Cl.
*A24F 47/00* (2006.01)
*A61M 15/00* (2006.01)
(Continued)

(52) U.S. Cl.
CPC ....... *A24F 47/002* (2013.01); *A61M 15/0091* (2013.01); *A61M 15/06* (2013.01);
(Continued)

(58) Field of Classification Search
None
See application file for complete search history.

(56) References Cited

U.S. PATENT DOCUMENTS

| | | | |
|---|---|---|---|
| 2011/0290248 A1* | 12/2011 | Schennum | A24F 47/002 128/202.21 |
| 2011/0290249 A1 | 12/2011 | Schennum | |
| 2012/0318827 A1 | 12/2012 | Schennum | |

FOREIGN PATENT DOCUMENTS

| | | |
|---|---|---|
| DE | 2307417 A1 | 10/1974 |
| DE | 4030257 A1 | 4/1992 |

(Continued)

OTHER PUBLICATIONS

Machine translation of DE2307417.*

(Continued)

*Primary Examiner* — Michael J Felton
*Assistant Examiner* — Katherine A Will
(74) *Attorney, Agent, or Firm* — Patterson + Sheridan, LLP

(57) ABSTRACT

A simulated cigarette having a generally cylindrical cigarette like housing with a main axis, the housing containing a reservoir of a pressurised inhalable composition. The reservoir has a reservoir outlet at one end which is selectively closed by an outlet valve. The simulated cigarette further comprises a tube with a through bore extending along a substantial portion of the reservoir from the vicinity of the reservoir outlet such that composition flows into a tube bore inlet and along the tube bore to the reservoir outlet. The tube inlet end is retained such that the axis passes through the inlet end and so that the tube bore inlet is positioned in the axial sense in the central 50% of the volume of the reservoir.

10 Claims, 2 Drawing Sheets

(51) Int. Cl.
    *A61M 15/06*     (2006.01)
    *B65D 83/32*     (2006.01)
    *B65D 83/42*     (2006.01)
    *B65D 83/36*     (2006.01)

(52) U.S. Cl.
    CPC ............. *B65D 83/32* (2013.01); *B65D 83/42* (2013.01); *B65D 83/36* (2013.01)

(56) References Cited

FOREIGN PATENT DOCUMENTS

| | | |
|---|---|---|
| EP | 0824927 A2 | 2/1998 |
| EP | 2614732 A1 | 7/2013 |
| WO | 2011107737 | 9/2011 |
| WO | 2012129787 A1 | 10/2012 |
| WO | 2014033438 A1 | 3/2014 |

OTHER PUBLICATIONS

Machine translation of DE4030257.*
International Search Report and Written Opinion dated Jul. 7, 2014 for Application No. PCT/GB2014/050939.
United Kingdom Search Report dated Sep. 19, 2013 for Application No. GB1305494.5.

* cited by examiner

SIMULATED CIGARETTE

The present invention relates to a simulated cigarette having a generally cylindrical cigarette like housing with a main axis, the housing containing a reservoir of a pressurised inhalable composition extending along a substantial portion of the housing, the reservoir having a reservoir outlet at one end which is selectively closed by an outlet valve, the outlet valve being operable to allow the composition to flow from the reservoir outlet to an inhalation outlet at the outlet end of the device. Such a simulated cigarette will subsequently be referred to as "of the kind described".

A simulated cigarette of the kind described is disclosed in WO2011/107737. This document requires a wick filling a substantial portion of the reservoir in order to ensure that adequate composition is provided to the reservoir outlet when the outlet valve is open.

It has been found, however, that the wick effectively strips nicotine out of the composition such that it provides an inconsistence dosage.

Another cigarette of the kind described is disclosed in DE4030257. One example in this document discloses a tube extending for a short distance from the outlet end of the reservoir. The tube is flexible and has a weight at its inlet end such that it is weighted towards the bottom face of the reservoir, whatever its orientation. Such an arrangement is designed to allow as much composition as possible to be inhaled from the reservoir. However, a problem with this design is that the amount of composition that is available for the user will depend upon the orientation of the cigarette. If the cigarette is used in a horizontal configuration, most of the composition can be inhaled. However, the most common way of inhaling from a cigarette is in a "tip-down" configuration in which the inhaling end of the cigarette is above the opposite end. In such an orientation, somewhere around half of the composition cannot be inhaled. For each use of the cigarette there will therefore be a large variation in the amount of composition inhaled by the user, depending on the orientation. High variation in dose is not desirable from a regulatory point of view, and for the user as they do not have a good idea of the quantity of nicotine that they have inhaled.

According to the present invention, a simulated cigarette of the kind described, comprises a tube with a through bore extending along a substantial portion of the reservoir from the vicinity of the reservoir outlet such that composition flows into a tube bore inlet and along the tube bore to the reservoir outlet, a tube inlet end being retained such that the axis passes through the inlet end and so that the tube bore inlet is positioned in the axial sense in the central 50% of the volume of the reservoir.

The volume of the reservoir is the free space inside the reservoir, namely the total volume that can be occupied by the composition. This volume excludes any internal features within the reservoir such as the tube wall. It does, however, include the volume of the tube bore. This volume can either be determined by calculating the volume of the various components (i.e. the internal volume of the reservoir housing minus the volume of any internal components), or can be determined by fully filling the reservoir with a liquid and measuring the volume of liquid required to do this (e.g. by determining the mass increase). By filling the reservoir with 50% of this volume and orientating the simulated cigarette with its axis vertical, the mid-point of the volume can be determined. This can be repeated with a volume of liquid which is 25% greater and 25% less respectively than the 50% volume referred to above. These two levels determine the central 50% of the volume of the reservoir as defined above. Alternatively, these positions can be calculated based on the volumes of the components.

By providing the tube bore inlet radially towards the centre of the reservoir, in a central portion of the volume in the axial sense, the tube bore inlet is in a position in which it is in the vicinity of the centroid of a body of liquid filling the reservoir such that, whatever the orientation of the cigarette, approximately 50% of the liquid can be dispensed.

Thus, it can be seen that the approach taken is different from that of DE4030257 in that the aim is to maximise the uniformity of the dosing, not to maximise the total amount of the dosing. This is achieved by retaining the inlet end of the tube in a central region of the reservoir, rather than having a flexible tube which is always biased towards the lowermost position.

Preferably, the tube bore inlet is positioned in the central 30% and more preferably 20% of the volume of the reservoir as this reduces variation still further.

While the tube bore inlet is in the central region of the reservoir as set out above, preferably, it is in the half of the volume furthest from the outlet. The 50%, 30% and 20% limits above allow the inlet to be 25%, 15% and 10% respectively from the centre of the reservoir. Given the desire to have the inlet towards the end opposite to the outlet end, the preferred range may be lower towards the outlet than the opposite end. It may, for example, be preferred to have the inlet with 15% of the centre of the volume towards the outlet end and 25% of the volume towards the opposite end. This allows a greater volume to be inhaled in the more common "tip-down" configuration, but is still sufficiently close to the centre that undue variation of the dosage is avoided.

The tube inlet may be retained in place by the tube being rigid enough that it can support itself with the tube bore inlet in the defined position. However, preferably, the tube is a flexible tube and a support is provided to retain the inlet end in position.

The support preferably has an outer diameter which can form an interference fit with an inner wall of the reservoir. The support preferably has a hollow conical end portion facing the inlet end of the tube to guide the inlet end into position. This allows for a straight forward assembly process as the tube can be pushed into the reservoir so that it engages with the inner wall of the reservoir adjacent to the reservoir outlet or the outlet valve itself. The support can then be fitted into place such that the conical end portion picks up the inlet end and guides it towards the central region.

The simulated cigarette may be a single use device. However, preferably, the reservoir is refillable and has a refill valve at a refill end opposite to the outlet end. In this case, the tube support is preferably integrated with a refill valve housing. This helps to reduce the number of components in the simulated cigarette.

The outlet valve may be manually operated, but is preferably a breath operated valve. The outlet valve is preferably biased closed by a resilient member and is supported by a flexible diaphragm, and an air flow path is provided through the cigarette such that suction on the outlet end causes the air flow to create a pressure on the diaphragm sufficient to lift the outlet valve against the action of the resilient member and open the outlet valve.

The inhalable composition preferably comprises nicotine and a propellant.

The tube is preferably relatively long and extends for at least 60% of the length of the cigarette. The bore is preferably less than 1 mm. Tubes with at least a portion of different internal diameters can be used in order to vary the dosage that the cigarette is able to dispense. Previously, the dosage was varied by varying the size of an outlet orifice downstream of the outlet valve, but this also changes the particle size. By using the bore to control the dosage, this can be done without compromising the particle size.

An example of a simulated cigarette in accordance with the present invention will now be described with reference to the accompanying drawings, in which.

Figure 1:
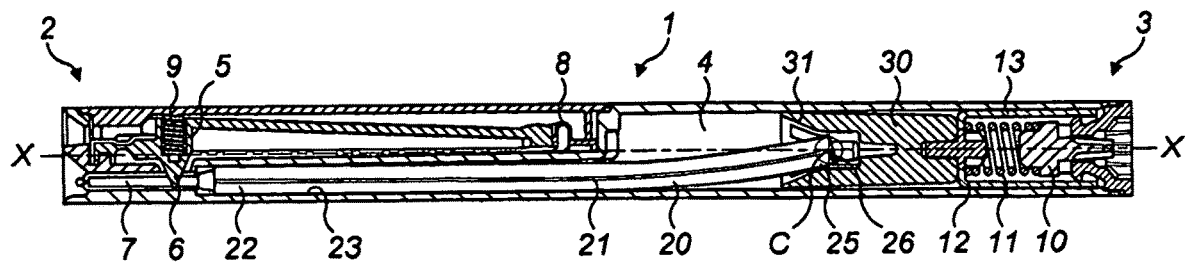
FIG. 1 is an axial cross section through the simulated cigarette.
Figure 2:
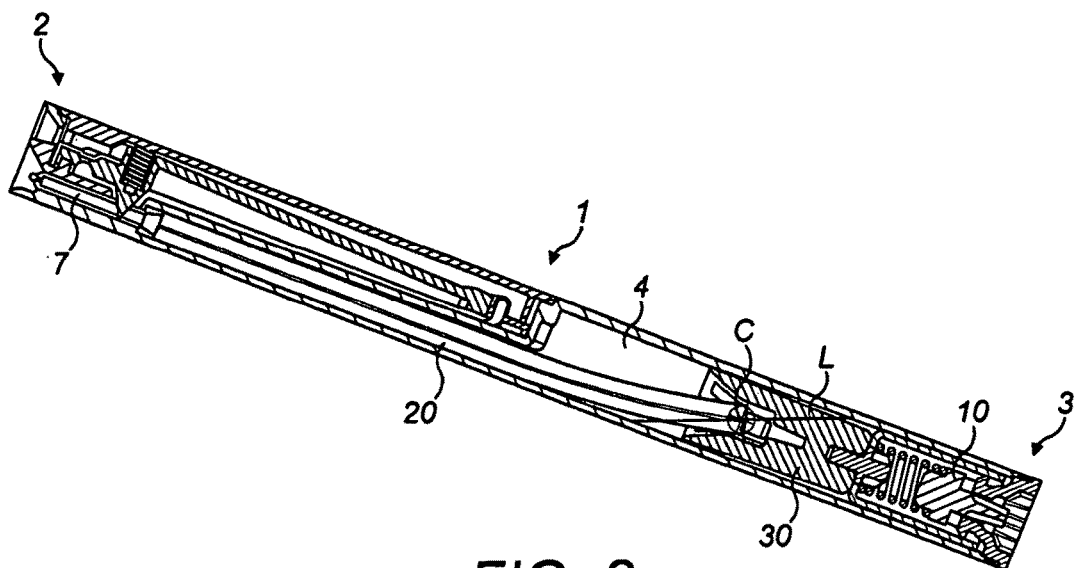
FIG. 2 is a view similar to FIG. 1 in a "tip-down" configuration.
Figure 3:
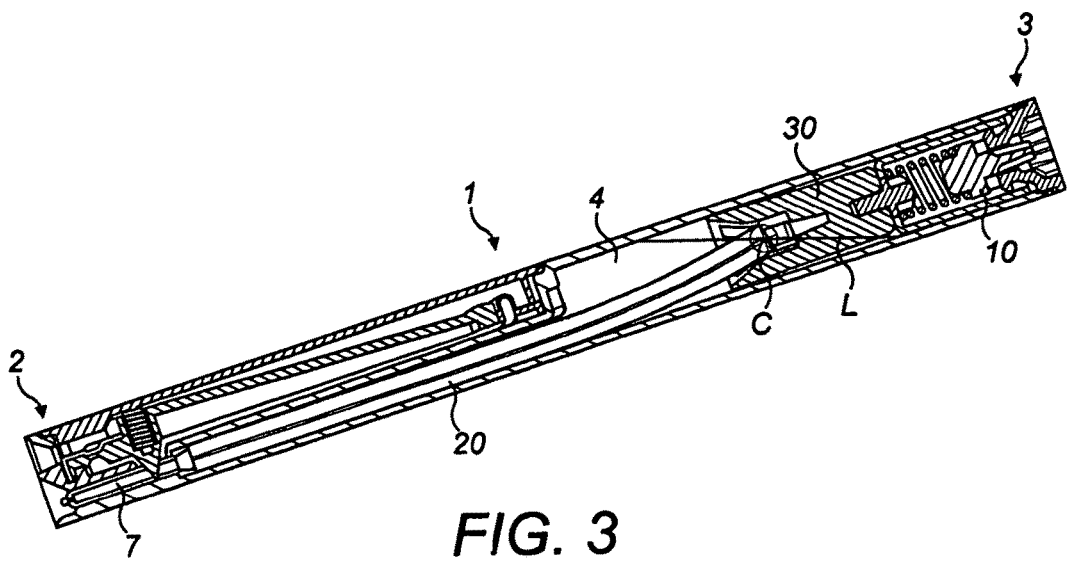
FIG. 3 is a view similar to FIGS. 1 and 2 in a "tip-up" configuration.
Figure 4:
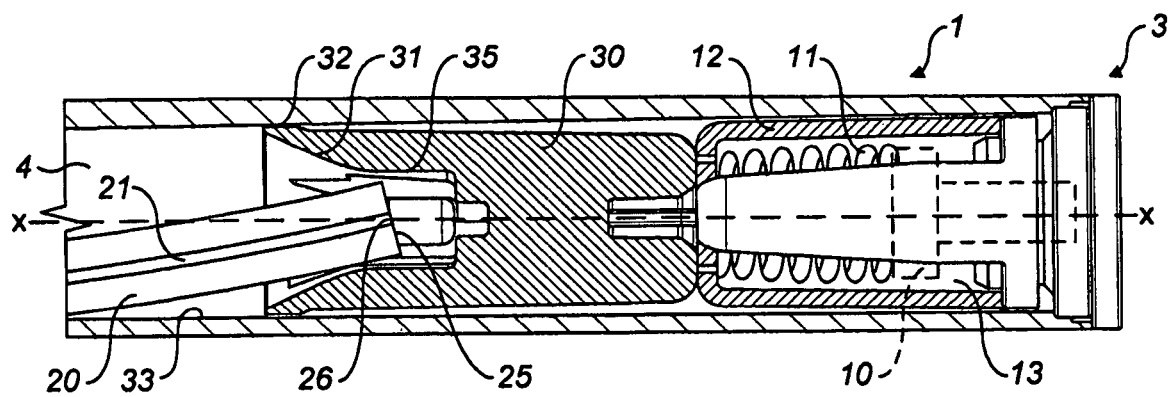
FIG. 4 is an axial cross section showing the right hand portion of FIG. 1 in greater detail.
Figure 5:
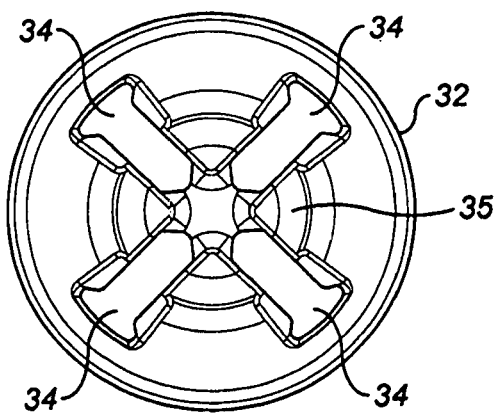
FIG. 5 is an end view of the tube support.

The basic arrangement of the simulated cigarette is as described in WO2011/107737. Thus, the simulated cigarette has a generally cylindrical shape and is approximately the size of a cigarette. It has a housing 1 with an outlet end 2 and a refill end 3 with a reservoir 4 occupying the majority of the internal space. At the outlet end 2 is an outlet valve 5 with a valve element 6 in the form of a tooth which pinches a resilient tube 7 in order to close the tube. The outlet valve 5 further comprises a vane which cooperates with a diaphragm 8 to open the valve element 6 against the action of a spring 9 when a user sucks on the outlet end 2 as described in WO2011/107737 and in greater detail in WO 2014/033438.

At the opposite end of the reservoir 4 is the refill valve element 10 which is essentially a check valve which is openable against the action of a second spring 11. This is the subject of co-pending application 1305486.1. The second spring 11 and refill valve element 10 are retained in a cage 12 which has a number of openings 13 such that the space within the cage 13 forms part of the reservoir 4.

Also within the reservoir 4 is a flexible tube 20 with an internal bore 21. The bore 21 has an outlet 22 located adjacent to the end of the resilient tube 7 and can be placed against or is sealed to the wall 23 of the reservoir 23 in the vicinity of the outlet end so that the composition can only reach the outlet valve 5 via the bore 21. As is apparent from the drawings, it can be either the side wall or the end wall of the tube 20 that seal with the wall 23 if the reservoir or the end of the tube 7, but it is preferably both. It will also be apparent from the drawings that the right hand side of the resilient tube 7 between the valve element 6 and the tube 20 is also a part of the reservoir.

At the inlet end 25 of the tube 20, the bore 21 has an inlet 26 which is supported by a support 30 so that the inlet end 25, and preferably the inlet 26 of the bore 21 is on the main axis X of the housing 1 as shown in FIG. 4.

The support 30 abuts against the valve cage 12 at the end of the support 30 closest to the refill end 3. The support 30 and valve cage 12 may be made as a single component. At the opposite end, the support 30 has a conical face 31 facing towards the outlet end 2. The outer diameter 32 of this end has a diameter corresponding to the internal diameter 33 of the reservoir 4 at this point so that the support 30 is an interference fit within the reservoir 4. Four openings 34 as shown in FIG. 5 allow the liquid in the reservoir to freely pass the support 30 to gain access to the inlet 26.

To assemble the cigarette, the tube 20 is inserted into the reservoir 4 until it reaches the position show in FIG. 1 in which the outlet 22 seals with the wall 23. The support 30 is then inserted from the same end and the conical face 31 picks up the inlet end 25 and guides it into a central region as shown in the drawings. The conical region 31 extends into a cylindrical region 35 which maintains the inlet end 25 of the tube 20 in the central region. The end of the tube may be tightly held in this position, or may be free to move a small amount which is immaterial to its ability to function. Even if it is tightly held, the openings 34 allow liquid in the reservoir to reach the inlet 26 of the bore 21.

It will be appreciated from the drawings and from the above explanation that the shape of the reservoir 4 is complex. The right hand portion has a generally cylindrical configuration occupying the majority of the diameter of the device while the left hand portion of the reservoir may just be the internal bore 21 of the tube, or there may be a portion of the reservoir on either side of this tube. Further, in the right hand portion, the volume of the reservoir is reduced by the inlet end portion of the tube 20, the support 30, the valve cage 12, the second spring 11 and the portion of the refill valve element 10 which is within the reservoir. Thus, while the volume of the reservoir 4 can be determined by measuring these components, it may be simpler to determine this experimentally.

The operation of the device will now be described with reference to FIGS. 1 to 3.

When a user sucks on the outlet end 2, the outlet valve 5 opens as previously described. Provided that the inlet 26 of the bore 21 is below the level L of the liquid in the reservoir, the liquid will travel along the bore 21 and will be atomised downstream of the outlet valve element 6 to create a plume for inhalation. FIGS. 1 to 3 show the centroid C of a body of liquid filling the reservoir 4. The inlet 26 of the bore 21 is in the vicinity of the centroid. In this specific example shown in FIG. 1, it is displaced by 1.3 mm from the centroid C towards the refill end 3. In the horizontal orientation shown in FIG. 1, all of the liquid above the level L which represents approximately 50% of the total liquid in the reservoir can be inhaled from the cigarette. When the cigarette is in the tip-down configuration shown in FIG. 2, as the inlet 26 is displaced from the centroid C as described above, slightly more liquid is available than it is in FIG. 1. Conversely, in the tip-up configuration, slightly less liquid is available for inhalation. In a different arrangement, the inlet 26 is at the centroid C, so that there is essentially no variation in dispensing between the three positions. The current preference is for a slight displacement of the inlet 26 towards the refill end from the centroid C as shown as this causes slightly more liquid to be dispensed in the more common tip-down orientation.

Once the cigarette reaches the liquid level position L shown in FIGS. 1 to 3 with the reservoir approximately half full, no further liquid can be inhaled and the cigarette is then refilled via the refill valve 10.

The invention claimed is:

1. A simulated cigarette having a generally cylinder-shaped cylindrical cigarette like housing with a main axis corresponding to a cylindrical axis of the cylinder shape, the housing containing a reservoir of a pressurized pressurised inhalable composition extending along a substantial portion of the housing, the reservoir having a reservoir outlet at one end which is selectively closed by an outlet valve, the outlet valve being operable to allow the composition to flow from the reservoir outlet to an inhalation outlet at the outlet end of the device; wherein the simulated cigarette further comprises a tube with a through bore extending along a substantial portion of the reservoir from the vicinity of the reservoir outlet such that composition flows into a tube bore inlet and along the tube bore to the reservoir outlet, a tube inlet end being retained such that the main axis passes through the inlet end and so that the tube bore inlet is positioned in the axial sense in the central 50% of the volume of the reservoir.

2. A simulated cigarette as claimed in claim 1, wherein the tube bore inlet is positioned in the central 30% and preferably the central 20% of the volume of the reservoir.

3. A simulated cigarette as claimed in claim 1, wherein the tube bore inlet is in the half of the volume furthest from the outlet.

4. A simulated cigarette as claimed in claim 1, wherein, the reservoir is refillable and has a refill valve at a refill end opposite to the outlet end.

5. A simulated cigarette as claimed in claim 1, wherein the outlet valve is a breath operated valve.

6. A simulated cigarette as claimed in claim 5, wherein the outlet valve is biased closed by a resilient member and is supported by a flexible diaphragm, and an air flow path is provided through the cigarette such that suction on the outlet end causes the air flow to create a pressure on the diaphragm sufficient to lift the outlet valve against the action of the resilient member and open the outlet valve.

7. A simulated cigarette as claimed in claim 1, wherein the inhalable composition comprises nicotine and a propellant.

8. A simulated cigarette as claimed in claim 1, wherein the tube extends for at least 60% of the length of the cigarette.

9. A simulated cigarette as claimed in claim 1, wherein the internal diameter of the bore is less than 1 mm.

10. A simulated cigarette having a generally cylinder-shaped cylindrical cigarette like housing with a main axis corresponding to a cylindrical axis of the cylinder shape, the housing containing a reservoir of a pressurized pressurised inhalable composition extending along a substantial portion of the housing, the reservoir having a reservoir outlet at one end which is selectively closed by an outlet valve, the outlet valve being operable to allow the composition to flow from the reservoir outlet to an inhalation outlet at the outlet end of the device; wherein the simulated cigarette further comprises a tube with a through bore extending along a substantial portion of the reservoir from the vicinity of the reservoir outlet such that composition flows into a tube bore inlet and along the tube bore to the reservoir outlet, a tube inlet end being retained such that the axis passes through the inlet end and so that the tube bore inlet is positioned in the axial sense in the central 50% of the volume of the reservoir, and wherein the tube is a flexible tube and a support is provided to retain the inlet end in position.

* * * * *